(12) United States Patent
Stoeckl

(10) Patent No.: US 7,785,007 B2
(45) Date of Patent: Aug. 31, 2010

(54) BITE DEVICE USED WITH A PANORAMA X-RAY DEVICE

(75) Inventor: Klaus Stoeckl, Bensheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 0 days.

(21) Appl. No.: 12/379,278

(22) Filed: Feb. 18, 2009

(65) Prior Publication Data

US 2009/0154656 A1 Jun. 18, 2009

Related U.S. Application Data

(63) Continuation of application No. 10/531,985, filed on Apr. 20, 2005, now Pat. No. 7,497,619.

(30) Foreign Application Priority Data

Oct. 25, 2002 (DE) .................... 102 50 005

(51) Int. Cl.
*H05G 1/00* (2006.01)

(52) U.S. Cl. .................. 378/204; 378/38; 378/208
(58) Field of Classification Search ............ 378/38–40, 378/168–170, 177, 178, 189, 191, 204, 205, 378/208
See application file for complete search history.

(56) References Cited

U.S. PATENT DOCUMENTS 2,123,210 A * 7/1938 Schantz ............... 378/170
6,118,842 A * 9/2000 Arai et al. ............ 378/39
6,424,694 B1 * 7/2002 Molteni et al. ........ 378/38

* cited by examiner

*Primary Examiner*—Jurie Yun
(74) *Attorney, Agent, or Firm*—Dykema Gossett PLLC

(57) ABSTRACT

A bite device for the correct positioning of a patient when a panoramic X-ray is taken, comprising a holder part which can be placed in a fixed direction in relation to the X-ray device, a plate which can pivot against the holder and which is provided with a bite part into which a patient bites, and means for detecting the pivoting angle A between the plate and the holder part.

2 Claims, 3 Drawing Sheets

BITE DEVICE USED WITH A PANORAMA X-RAY DEVICE

BACKGROUND OF THE INVENTION

The invention relates to a system for correct positioning of a patient when the latter is X-rayed with a medical panoramic X-ray device.

PRIOR ART

When recording a panoramic X-ray image, the tomography zone ideally runs through the alveolar ridge of the patient. In order to achieve a high degree of recording quality, it is necessary to bring these two elements, tomography zone and alveolar ridge, into the best possible spatial relationship. In the panoramic X-ray device, the tomography zone can be adjusted to the individual shape and position of the jaw of a patient within certain limits. The condition is, however, that these are known to the operator. In particular, knowledge of the following features is significant:
 the spatial orientation of the edge-to-edge occlusal plane (bite plane) relative to a reference point on the panoramic X-ray device; and
 the individual anatomic characteristics of the jaw: its size, shape, anomalies and the like.

Traditionally, the patient's head is fixed in position relative to the device for taking a panoramic radiograph by means of a patient's head positioner comprising a forehead pad and/or ear pads, a bite block, a nasion, or a chin pad. The necessary alignment of the head is usually achieved with the aid of optical lines projected onto the patient's head and depicting the Frankfurt horizontal and median planes. The Frankfurt horizontal plane runs through the right and left porion, the highest point of the meatus acusticus externus, and the orbital, which represents the lowest point of the osseous edge of the orbita. The projected median plane runs as a sagittal plane from the crown of the head through the center of the nose to the chin. It assists symmetrical positioning of the head.

The position of the occlusal plane is not directly registered but only indirectly by way of the Frankfurt horizontal plane. To this end, the Frankfurt horizontal plane projected onto the patient's head by the panoramic X-ray device and the incisal teeth in the edge-to-edge bite are used to derive the position of the occlusal plane. The correlation between the occlusal plane and the Frankfurt horizontal plane is generally acknowledged from an anatomical standpoint, but positioning errors relative to the Frankfurt horizontal plane of the patient cannot be excluded.

In order to determine the individual size of the patient's jaw, a frontal diameter measurement may be carried out, if necessary. Derivation of the jaw size is not, however, sufficiently reliable.

Neither has any reliable system been as yet developed for determining the shape of the alveolar arch or any anomalies of the jaw.

Present-day panoramic X-ray devices, therefore, offer only a few modification options, since the operator could not in any case make use of such adjustment options due to insufficient knowledge of the individual form of a patient's jaw.

This forms the basis of the invention. It is an object of the invention, as characterized in the claims, to provide a system for correct positioning of a patient for image recording using a medical panoramic X-ray device, which allows for simple and stable measurement and/or adjustment of the inclination of the occlusal plane of a patient.

DESCRIPTION OF THE INVENTION

This object is achieved, according to the invention, by the bite device defined in claim 1. Advantageous embodiments of the invention are subject matter of the sub-claims.

The invention improves on the prior art in that a bite device includes a holding member held in a directionally fixed position relative to the X-ray device, and a plate which is pivoted relative to the holding member and which has a bite piece on which the patient bites. The bite device also includes means for measuring the angle of deflection $\alpha$ between the plate and the holding member, which means for measuring the angle of deflection $\alpha$ are located in a zone of the bite device which is free from radiation during X-ray imaging. The zone involving X-ray irradiation can therefore be kept substantially free from metal.

The invention is thus based on the idea of measuring the position of the occlusal plane of the patient relative to the device by determining the position of a plate disposed in the occlusal plane. For this purpose, the angle is measured between the plate and a holding member, which can be positioned relative to the X-ray device in fixed alignment. From this angle a signal can be derived which indicates the degree of inclination of the occlusal plane.

It is advantageous for the means for measuring the angle of deflection a to contain one or more sensors located in the holding member. For example, the sensors might be in the form of a photoelectric sensor located in the holding member and adapted to register the position of an opening that is moved upwardly and downwardly in accordance with the pivotal motion of the plate.

The bite device of the invention can conveniently include means for displaying the angular position of the pivoted plate.

In a preferred development of the bite device, there are further provided driving means for vertical adjustment of the holding member and thus for pivoting the plate into a predetermined angular position. This makes it possible to adapt to the patient's body size, and the patient can be constrained to adjust the inclination of his head to the inclination of the plate, so that a desired angular position of the patient's occlusal plane relative to the X-ray device will be achieved.

It is advantageous for the plate-swinging means to move the plate to the predetermined angular position automatically and to stop when the predetermined angular position has been reached.

Alternatively or additionally, provision may be made for said means to indicate that the predetermined angular position of the plate has been reached by emitting optical and/or acoustic signals.

In a preferred embodiment of the bite device of the invention, the pivoted plate is connected to a rail within the holding member, which rail can be moved upwardly and down-wardly and has an opening for indicating the position of the rail in the holding member.

The bite piece of the bite device is preferably equipped with a replaceable protective sheath for hygienic reasons.

Alternatively, the bite piece can be in the form of a replaceable bite piece. The bite piece is preferably composed of a soft material, particularly a substantially radiolucent material. It has proved to be particularly suitable to fabricate the bite piece from closed-cell ethylene foam.

The bite piece preferably occupies an angular range $\beta$ of the mandibular arch, which is between 20° and 40°, particularly 30°. This substantially prevents any sideways tipping or tilting of the patient's head.

In an advantageous embodiment, the bite piece has on its upper surface and on its undersurface a bite groove to accommodate part of the dental arch of the patient's upper and lower jaw respectively.

The bite piece is preferably a unitary piece foldable about a folding edge. It preferably has on opposite sides a wedge-shaped projection and a complementary depression for the accommodation of said projection, to enable the bite piece to be removably attached to the pivoted plate.

Further advantageous embodiments, features, and details of the invention are given in the dependent claims, the description of embodiments, and the drawings.

BRIEF DESCRIPTION OF THE DRAWINGS

The invention will now be explained in more detail with reference to an embodiment and the drawings. Only those elements are shown which are significant for comprehension of the invention.

In the drawings.

DESCRIPTION OF EMBODIMENTS

Figure 1:
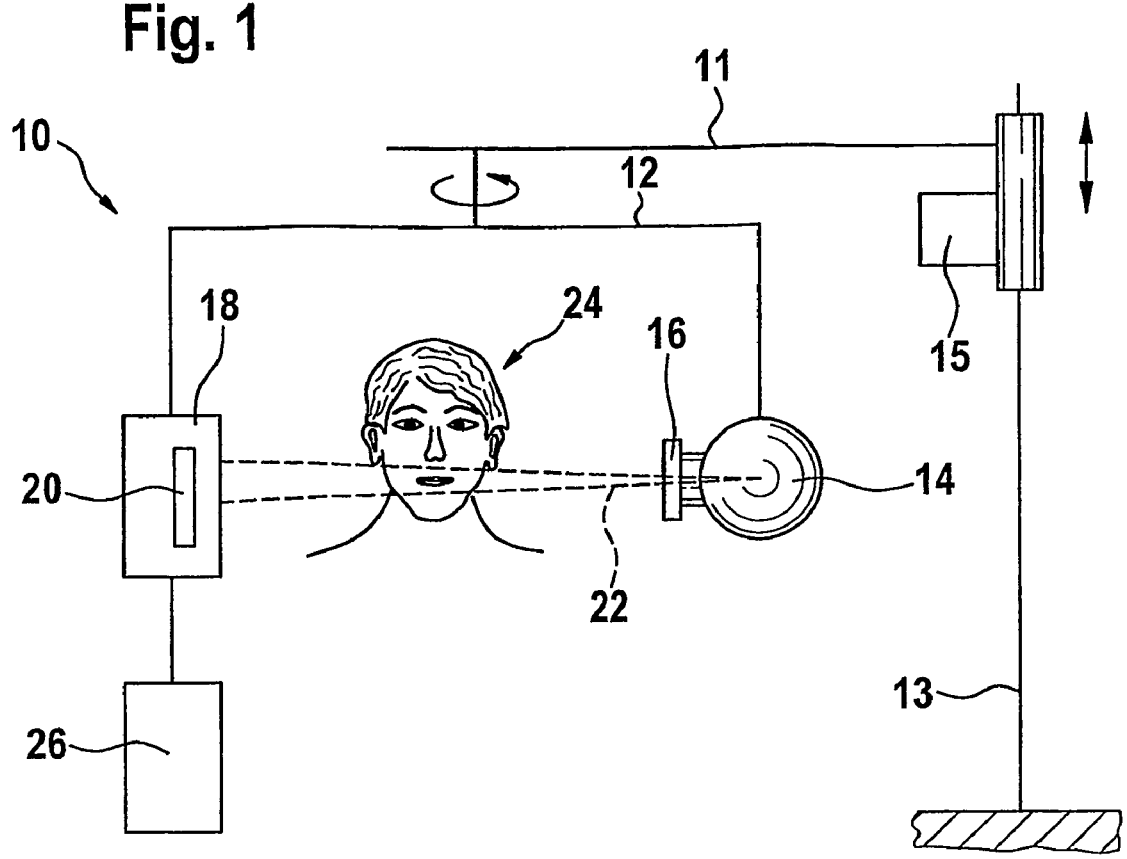
FIG. 1 is a diagrammatic illustration of a panoramic X-ray system.

FIG. 1 is a diagrammatic representation of a panoramic X-ray system 10, in which a rotary unit 12 carries a radiation source 14 equipped with a shutter 16, and a diametrically opposed detector camera 18 equipped with a shutter 20. The beam of X-rays 22 emitted from the radiation source 14 transilluminates the jaw region of the head 24 of a patient and produces an image signal in detector camera 18. This is directed to a control unit 26 for evaluation and display in the usual manner.

Figure 2:
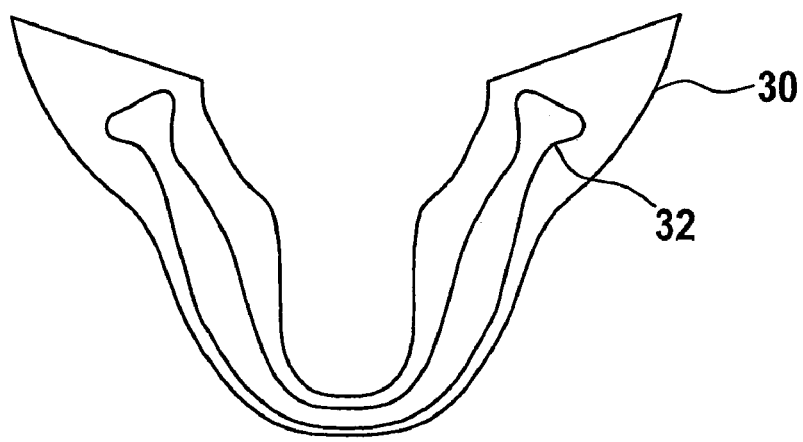
FIG. 2 is a diagrammatic representation of the system for aligning the tomography zone of the X-ray device to the alveolar arch of a patient.

Rotary unit 12 is pivotally or hingedly mounted on an arm 11 which is mounted on a column 13 for vertical adjustable thereon. A drive 15 is provided to perform the vertical adjustment. In this way, the position of X-ray emitter 14 and detector camera 18 can be adjusted to the stature of the patient. It is essential, for obtaining a faultless, high-quality panoramic radiograph, for the tomography zone 30 (FIG. 2) to be in line with the alveolar arch 32 of the patient. FIG. 2 depicts perfect spatial alignment of these two elements, this ensuring the production of a qualitatively good image. Insufficient alignment can necessitate a repeat radiograph, resulting in increased X-irradiation of the patient and additional expense in terms of material and time.

Figure 3:
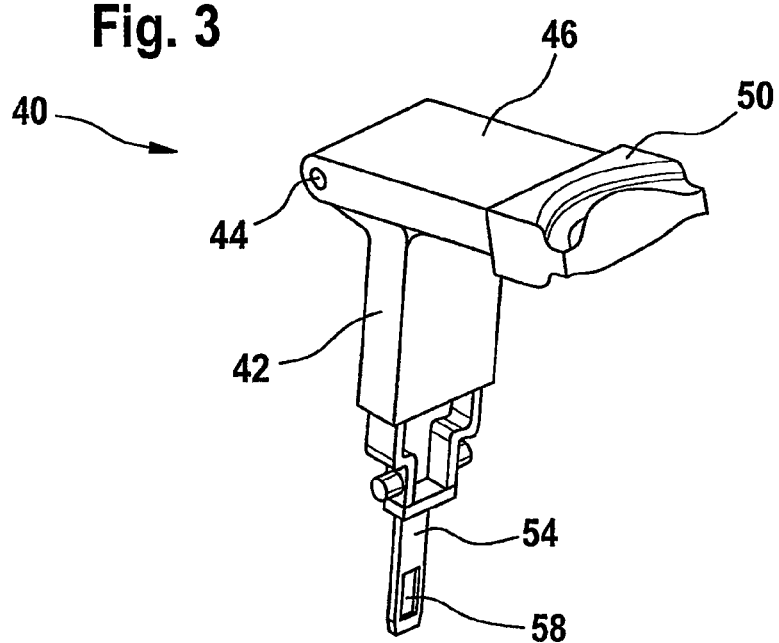
FIG. 3 shows a perspective view of a bite device according to one embodiment of the invention, shown diagrammatically.
Figure 4:
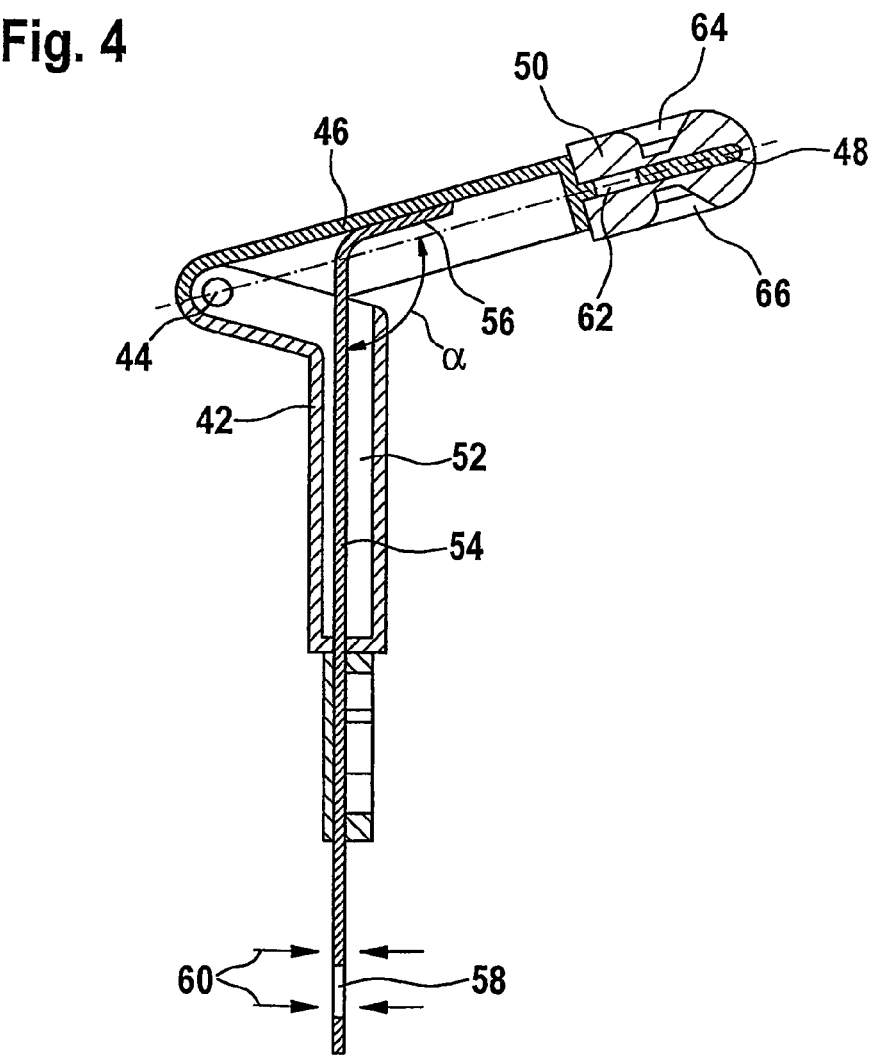
FIG. 4 is a cross-section through the bite device of FIG. 3.

FIG. 3 is a perspective view of a bite device referenced as 40, according to one embodiment of the invention, shown diagrammatically, and FIG. 4 is a cross-section through the bite device 40 of FIG. 3. Bite device 40 has a holder 42 which is hinged to a thin plate 46 by means of a pivot 44. The thin plate 46 is adjoined, at its end remote from pivot 44, by an imaging zone 48 parallel to said thin plate.

The imaging zone 48 has an opening 62 by means of which, in a manner to be described in more detail below, a replaceable bite piece 50 can be quickly and easily attached to the thin plate. On its upper surface and on its undersurface, bite piece 50 has occlusal grooves 64 and 66 respectively, which accommodate the dental arches of the patient's upper and lower jaw respectively. This arrangement ensures that the thin plate 46 runs parallel to the occlusal plane of the patient when he bites on the bite piece 50 for taking the radiograph.

The angle of deflection a of thin plate 46 is measured using a rail 54 capable of being moved upwardly and down-wardly and connected to thin plate 46 in a region 56, and adapted to extend vertically down the inside 52 of the holding member 42. In its lower section, rail 54 is provided with a hole 58. The vertical position of hole 58 is detected by two photodetectors indicated by arrows 60. The angle of deflection of plate 46 can be deduced from said vertical position. By transferring the inclination of plate 46 to the movable rail, measurement of the angle of deflection a is carried out in a region of holder 42 which is far below plate 46 and is free from radiation. The X-irradiated region can thus be kept substantially free from metal.

The bite device cooperates with a driving system 15 shown in FIG. 1 such that rail 54 moves upwardly or downwardly and the thin plate 46 can thus be brought into any desired position. The deflection of thin plate 46 accompanying such vertical adjustment makes it possible to gently guide the patient's head until it assumes the correct degree of inclination for the panoramic radiograph.

Vertical adjustment of plate 46 can be performed interactively by the operator. For example, the operator can press an adjustment button until the desired degree of inclination is attained. When a previously defined angular position, for example α=105°, which corresponds to an angle between plate 46 and the horizontal of 15°, is attained, this can be indicated by means of optical and/or acoustic signals.

Alternatively, the drive can automatically move plate 46 into the predetermined angular position and stop when the desired position is reached. Additionally, the angular position of the plate can be displayed for checking by the operator.

Figure 5:
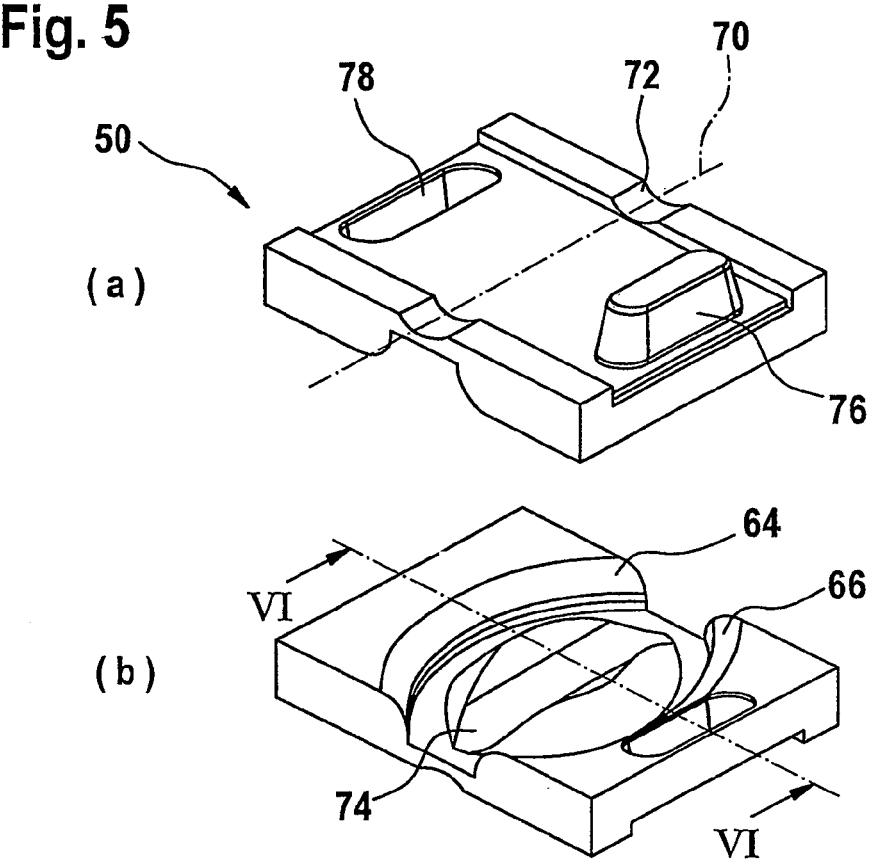
FIG. 5 shows perspective views of an bite piece for a bite device according to one embodiment of the invention, shown (unfolded) diagonally from below in FIG. 5(a) and diagonally from above in FIG. 5(b)
Figure 6:
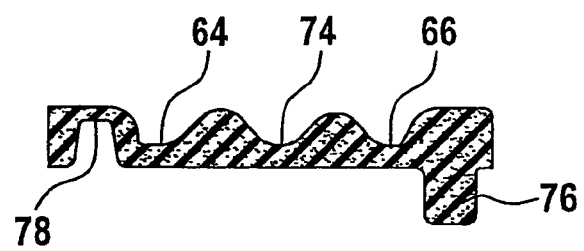
FIG. 6 is a cross-section through the bite piece of FIG. 5, taken along line VI-VI.

The bite piece 50 shown in FIGS. 3 and 4 will now be described in more detail with reference to FIGS. 5 through 7. FIG. 5 shows, in FIG. 5(a) and FIG. 5(b), a perspective view of the unfolded insert, shown diagonally from below in FIG. 5(a) and diagonally from above in FIG. 5(b). FIG. 6 shows a cross-section through the bite piece taken along line VI-VI of FIG. 5(b), and FIG. 7 represents the bite piece in the folded position, as attached to the bite device of FIG. 3.

In the present embodiment, bite piece 50 is fabricated as a single piece of closed-cell ethylene foam, a soft and substantially radiolucent material. On its upper surface, bite piece 50 has occlusal grooves 64 and 66 adapted to accommodate part of the dental arch of the upper and lower jaws of the patient. Bite piece 50 can be folded along a central folding edge 70, defined by notches 72 on the undersurface and a central groove 74 on the upper surface of the insert.

On its underside, bite piece 50 has a wedge-like tapered projection 76 which, when the insert is folded, slides into a complementary depression 78 located on the opposite side of the insert, this making for a stable but easily releasable connection. The flat imaging zone 48 of the bite device contains an opening 62 (FIG. 4) through which the projection 76 projects when the bite insert is attached, so that insert 50 is firmly attached to the thin plate 46 of the bite device once it has been folded together. After use, however, the insert can be unfolded with no great effort and thrown away for hygienic reasons.

Figure 7:
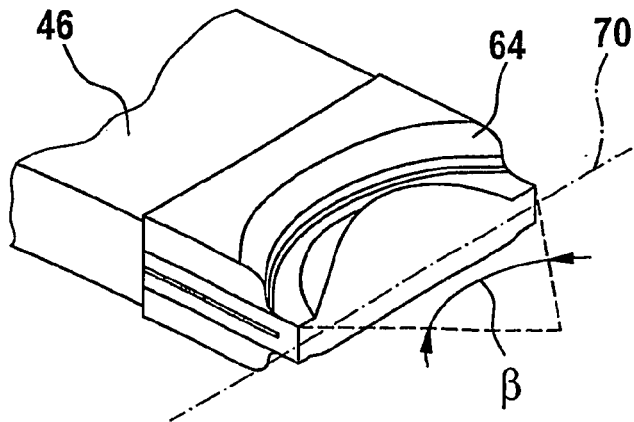
FIG. 7 shows the bite piece of FIG. 5 in the folded position, as attached to the bite device of FIG. 3.

The insert shown in the embodiment illustrated in FIGS. 5 through 7, has a width of 40 mm, occupies an angular region β of the dental arch of about 30°. In order to accommodate for different jaw sizes of patients, bite pieces are also fabricated and used in other widths. The different widths can be easily distinguished by the user on the basis of different color markings or other labels. With this kind of bite piece, the position of the patient can be fixed with great accuracy but without discomfort for the patient.

LIST OF REFERENCE NUMERALS OR CHARACTERS

10 radiographic system
12 unit
14 source of radiation
15 driving system
16 shutter
18 detector camera
20 shutter
22 beam of X-rays
24 head
26 evaluation unit
30 tomography zone
32 alveolar arch
40 occlusal device
42 holder
44 pivot
46 plate
48 imaging zone
50 bite piece
52 interior of holding member 42
54 rail
56 region
58 hole
60 arrows
62 opening
64 occlusal groove
66 occlusal groove
70 folding edge
72 notches
74 central groove
76 projection
78 depression

The invention claimed is:

1. A bite device for correct positioning of a patient into a predefined angular position for taking a radiograph with a panoramic X-ray device, comprising:
a holding member; a plate pivotally attached to said holding member, said plate including a bite piece on which the patient bites;
means for detecting an angle of deflection α between said plate and said holding member, and
driving means for vertically adjusting said holding member and thus pivot said plate.

2. A bite device as defined in claim 1, wherein said driving means pivots said plate automatically and stops when the angle of deflection α is detected and said predefined angular position is attained.

* * * * *